United States Patent [19]

Kung

[11] Patent Number: 5,320,825
[45] Date of Patent: Jun. 14, 1994

[54] SEROTONIN REUPTAKE INHIBITORS FOR S.P.E.C.T. IMAGING

[75] Inventor: Hank F. Kung, Wynnewood, Pa.

[73] Assignee: Trustees of the University of Pennsylvania, Philadelphia, Pa.

[21] Appl. No.: 694,346

[22] Filed: May 1, 1991

[51] Int. Cl.$^5$ .................. A61K 49/02; C07C 93/08
[52] U.S. Cl. .................. 424/1.85; 564/347; 564/353; 424/1.65
[58] Field of Search .................. 424/1.1; 564/347, 346, 564/354, 353; 514/651

[56] References Cited

U.S. PATENT DOCUMENTS

| | | | |
|---|---|---|---|
| 4,194,009 | 3/1980 | Molloy et al. | 514/651 |
| 4,296,126 | 10/1981 | Nedelac et al. | 514/651 |
| 4,313,896 | 2/1982 | Molloy et al. | 564/347 X |
| 4,314,081 | 2/1982 | Molloy et al. | 564/347 |
| 4,584,404 | 4/1986 | Molloy et al. | 514/651 X |
| 4,692,469 | 9/1987 | Watthey | 514/651 |
| 4,885,153 | 12/1989 | Wilbur et al. | 424/1.1 |

FOREIGN PATENT DOCUMENTS

| | | |
|---|---|---|
| 193405A1 | 3/1986 | European Pat. Off. . |
| 391554 | 10/1990 | European Pat. Off. . |
| 1593890 | 8/1973 | Fed. Rep. of Germany . |
| 2455571 | 1/1981 | France . |
| 90/11093 | 10/1990 | PCT Int'l Appl. . |
| 2060618 | 5/1981 | United Kingdom . |

OTHER PUBLICATIONS

Andrews, P., et al., "A Pharmacophore Hypothesis for Antidepressant Activity", Quant. Struct. Act. Relat. 6:97-103 (1987).
Angel, I., et al., "Anorectic Activities of Serotonin Uptake Inhibitors: Correlation with their Potencies at Inhibiting Serotonin Uptake In Vivo and $^3$H-Mazindol Binding In Vitro", Life Sci. 43:651-658 (1988).
Bäckström, I., et al., "High Affinity [$^3$H]Paroxetine Binding to Serotonin Uptake Sites in Human Brain Tissue", Brain Res. 486:261-268 (1989).
Benfield, P., et al., "Fluoxetine. A Review of Its Pharmacodynamic and Pharmacokinetic Properties, and Therapeutic Efficacy in Depressive Illness", Drugs 32:481-508 (1986).

(List continued on next page.)

Primary Examiner—Robert L. Stoll
Assistant Examiner—John M. Covert
Attorney, Agent, or Firm—Woodcock Washburn Kurtz Mackiewicz & Norris

[57] ABSTRACT

Disclosed are novel compounds for CNS neurotransmitter systems, especially for the neurotransmitter serotonin, which have the formula

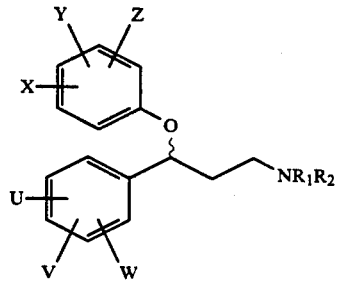

where each of U, V, W, X, Y and Z is independently selected from the group consisting of hydrogen; halogen; $C_1$-$C_4$ alkyl; $C_1$-$C_4$ alkyl substituted with one or more moieties selected from halogen atoms and hydroxy groups; $C_1$-$C_4$ alkoxy; $C_1$-$C_4$ alkoxy substituted with one or more moieties selected from halogen atoms and hydroxy groups; $C_1$-$C_6$ heterocycles; $C_1$-$C_4$ thioalkyl; $NR_3R_4$; —$R_5$—A—$R_6$; and —A—$R_7$; CN; $SO_2R_8$; —$NHCONH_2$; and $C(O)NR_3R_4$;
each of $R_1$, $R_2$, $R_3$ and $R_4$ is independently selected from the group consisting of hydrogen and $C_1$-$C_4$ alkyl;
each of $R_5$ and $R_6$ is independently a $C_1$-$C_6$ alkyl;
$R_7$ is selected from the group consisting of H, $C_1$-$C_6$ alkyl, $C_1$-$C_6$ heterocycles or —A—$R_5$;
$R_8$ is selected from the group consisting of $C_1$-$C_4$ alkyl and $NR_3R_4$;
A is selected from the group consisting of S, N and O;
provided that at least one of U, V, W, X, Y and Z is a halogen atom;
and pharmaceutically acceptable salts thereof.

16 Claims, 3 Drawing Sheets

OTHER PUBLICATIONS

Bogeso, K., "Neuroleptic Activity and Dopamine-Uptake Inhibition in 1-Piperazino-3-phenylindans", *J. Med. Chem.* 26:935-947 (1983).

Bogeso, K., et al., "3-Phenyl-1-indanamines. Potential Antidepressant Activity and Potent Inhibition of Dopamine, Norepinephrine, and Serotonin Uptake", *J. Med. Chem.* 28:1817-1828 (1985).

Coutts, R., et al., "Implications of Chirality and Geometric Isomerism in Some Psychoactive Drugs and Their Metabolites." *Chirality* 1:99-120 (1989).

Dannals, R., et al., "Synthesis of a Selective Serotonin Uptake Inhibitor: [$^{11}$C]Citalopram." *Int. J. Radiat. Appl. Intrum.*, Part A, 41(6):541-543 (1990).

DeSouza, E., "Autoradiographic Localization of $^3$H-Paroxetine Labeled Serotonin Uptake Sites in Rat Brain." *Synapse*, 1:488-496 (1987).

Fowler, J., et al., "New Directions in Positron Emission Tomography." *Ann. Rep. Med. Chem.* 24:277-286 (1989).

Frazer, A., et al., "Subtypes of Receptors for Serotonin." *Ann. Rev. Pharmacol. Toxicol.* 30:307-348 (1990).

Fuller, R., et al., "Effect of Fluoxetine Pretreatment on Plasma and Tissue Concentrations of Desipramine in Rats." *Res. Commun. Chem Pathol. Pharmacol.* 66:375-384 (1989).

Fuller, R., et al., "Fluoxetine: A Serotonergic Appetite Suppressant Drug." *Drug Dev. Res.* 17:1-15 (1989).

Gao, Y., et al., "Asymmetric Synthesis of Both Enantiomers of Tomoxetine and Fluoxetine." Selective Reduction of 2,3 Epoxycinnamyl Alcohol with Red-Al. *J. Org. Chem. 53:4081-4084 (1988).*

Goudie, A., et al., "Paroxetine, a Selective 5-Hydroxytryptamine Uptake Inhibitor with Antidepressant Properties, Lacks Amphetamine-like Stimulus Properties in an Operant Drug Discrimination Bioassay in Rodents." *J. Pharm. Pharmacol.* 40:192-196 (1988).

Graham, D., et al., "A Common Binding Site for Tricyclic and Nontricyclic 5-Hydroxytryptamine Uptake Inhibitors at the Substrate Recognition Site of the Neuronal Sodium-dependent 5-Hydroxytryptamine Transporter." *Biochem. Pharmacol.* 38:3819-3826 (1989).

Guan, X., et al., "Fluoxetine Increases the Extracellular Levels of Serotonin in the Nucleus Accumbens." *Brain. Res. Bull.* 21:43-46 (1988).

Habert, E., et al., "Characterization of $^3$H-Paroxetine Binding to Rat Cortical Membranes." *Eur. J. Pharmacol.* 118:107-114 (1985).

Hall, H., et al., "Effects of Zimelidine on Various Transmitter Systems in the Brain." *Adv. Biochem Psychopharmacol.* 31:321-325 (1982).

Hara, T., et al., "$^3$H-Paroxetine and $^3$H-Imopramine Binding to Rat Neuronal and Human Platelet Membranes." *Neurosci.* 14:117-119 (1988).

Hashimoto, K., et al., "In Vivo Labeling of 5-Hydroxytryptamine Uptake Sites in Mouse Brain with [$^3$H]-6-Nitroquipazine." *J. Pharm. Exp. Ther.* 255(1):146-153 (1990).

Hisrich, K., et al., "Fluoxetine." *J. Pharm. Technol.* 3:219-222 (1987).

Högberg, T., et al., "Stereoconservative Reductive Methyl-and Dimethylamination of Isomeric 3,3-Diarylpropenais. Synthetic and Mechanistic Studies on Control of the Stereochemistry." *J. Org. Chem.* 49:4209-4214 (1984).

Huang, S., et al., "Neuroreceptor Assay with Positron Emission Tomography: Equilibrium Versus Dynamic Approaches" *J. Cereb. Blood Flow Metab.* 6:515-521 (1986).

Huang, S., et al., "Quantitation in Positron Emission Tomography: 8. Effects of Nonlinear Parameter Estimation on Functional Images." *J. Comp. Asst. Tomogr.* 11(2): 314-325 (1987).

Hyttel, J., et al. "Neurochemical Profile of Lu 19-005, a Potent Inhibitor of Uptake of Dopamine, Noradrenaline, and Serotonin. *J. Neurochem.* 44:1615-1622 (1985).

Ives, J., et al., "Antidepressant Agents." *Ann. Rep. Med. Chem.* 24:21-29 (1989).

Johnson, A., "An Overview of the Animal Pharmacology of Paroxetine. *Acta Pyschiatr. Scand.* 350:14-20 (1989).

Kessler, R., et al. "Epidepride: A Selective and Very Potent Ligand for SPECT Imaging of the Dopamine D2 Receptor." *J. Nucl. Med.* 31:882 (1990).

Langer, S., et al., "Association of [$^3$H]-Imipramine and [$^3$H]-Paroxetine Binding with the 5HT Transporter in Brain and Platelets: Relevence to Studies in Depression." *J. Recept. Res.* 7:499-521 (1987).

(List continued on next page.)

OTHER PUBLICATIONS

Laruelle, M., et al., "Regional Distribution of Serotonergic Pre- and Postsynaptic Markers in Human Brain." *Acta Psychiatri. Scand.* 350:56–59 (1989).

Lasne, M., et al., "The Radiosynthesis of [N-methyl-$^{11}$C]-Sertraline." *Int. J. Radiat. Appl. Intrum.* Part A, 40(2):147–151 (1989).

Lassen, J., "Introduction to the Development of Paroxetine, a Novel Antidepressant." *Acta. Psychiatr. Scand.* 350:13 (1989).

Logan, J., et al., "Kinetic Modeling of Receptor-Ligand Binding Applied to Positron Emission Tomographic Studies with Neuroleptic Tracers." *J. Neurochem.* 48:73–83 (1987).

Marcusson, J., et al., "Dissociation Kinetics of [$^3$H]Paroxetine Binding to Rat Brain Consistent with a Single-Site Model of the Antidepressant Binding-/5-Hydroxytryptamine Uptake Site." *J. Neurochem.* 51:1477–1481 (1988).

Marcusson, J., et al., "Charactrerization of [$^3$H]Paroxetine Binding in Rat Brain", *J. Neurochem.* 50:1783–1790 (1988).

Mathis, C., et al., "High Affinity Aryl-Substituted [F-18] Fluoroalkylbenzamides for PET D-2 Studies." *J. Nucl. Med.* 31:737 (1990).

Munson, P., et al., "Ligand: A Versatile Computerized Approach for Characterization of Ligand-Binding Systems." *Anal. Biochem.* 107:220–239 (1980).

Oberlender, R., et al., "Tomoxetine and the Stereoselectivity of Drug Action." *J. Pharm. Pharmacol.* 39:1055–1056 (1987).

Pascali, C., et al., "The Radiosynthesis of NCA [O-Methyl$^{11}$C]Viqualine, through an N-Trityl-Protected Intermediate, as a Potential PET Radioligand for 5HT Re-uptake Sites." *J. Lab. Compd. Radiopharm.* 28:1341–1350 (1990).

Pascali, C., et al., "Citalopram: Labelling with $^{11}$C and Evaluation in Rat as a Potential PET Radioligand for 5-HT Re-uptake Sites." Abstract. *in Eight International Symp. Radiopharm. Chem.* Princeton, N.J.:392–393 (1990).

Perlmutter, J., et al., "Strategies for In Vivo Measurement of Receptor Binding Using Positron Emission Tomography.[ *J. Cereb. Blood Flow Metab.* 6:154–169 (1986).

Plenge, P., et al., "The Activity of 25 Paroxetine/-Femoxetine Structure Variants in Various Reactions, Assumed to be Important for the Effect of Antidepressants." *J. Pharm. Pharmacol.* 39:877–882 (1987).

Ram, S., et al., "Synthesis of [$^{11}$C]Citalopram and Brain Distribution Studies in Rats." Abstract. in Eighth International Symp. *Radiopharm. Chem.* Princeton N.J. :405–407 (1990).

Robertson, D., et al., "Synthesis of $^{14}$C and $^3$H-Labeled Fluoxetine, A Selective Serotonin Uptake Inhibitor." *J. Lab. Compd. Radiopharmaceuticals* 24(11):1397–1404 (1987).

Robertson, D., et al., "Molecular Structure of Fluoxetine Hydrochloride, a Highly Selective Serotonin-Uptake Inhibitor." *J. Med. Chem.* 31:185–189 (1988).

Rudorfer, M., et al., "Antidepressants: A Comparative Review of the Clinical Pharmacology and Therapeutic Use of the 'Newer' Versus the 'Older' Drugs." *Drugs.* 37:713–738 (1989).

Scheffel, U., et al., "In Vivo Labeling of Serotonin Uptake Sites with [$^3$H]Paroxetine." *J. Neurochem.* 52:1605–1612 (1989).

Scheffel, U., et al., "Evaluation of $^{11}$C-Citalopram and $^{11}$C-Fluoxetine as In Vivo Ligands for the Serotonin Uptake Site." Abstract. *J. Nucl. Med.* 31:833–834 (1990).

Srebnik, M., et al., "Chiral Synthesis via Organoboranes. 18. Selective Reductions. 43. Diisopinocampheylchloroborane as an Excellent Chiral Reducing Reagent for the Synthesis of Halo Alcohols of High Enantiomeric Purity. A Highly Enantioselective Synthesis of Both Optical Isomers of Tomoxetine, Fluoxetine, and Nisoxetine." *J. Org. Chem.* 53:2916–2920 (1988).

Tremaine, L., et al., "Metabolism and Disposition of the 5-Hydroxtryptamine Uptake Blocker Sertraline in the Rat and Dog." *Drug Metab. Dispos.* 17(5):542–550 (1989).

Wagner Jr., H., "Quantitative Imaging of Neuroreceptors in the Living Human Brain." *Sem. Nucl. Med.* 16(1):51–62 (1986).

Welch, M., et al., "Comparison in Animal Models of $^{18}$F-Spiroperidol and $^{18}$F-Haloperidol: Potential Agents for Imaging the Dopamine Receptors." *Life Sci.* 33:1687–1693 (1983).

Wong, D., et al., "Quantification of Neuroreceptors in the Living Human Brain. I. Irreversible Binding of Ligands." *J. Cereb. Blood Flow Metab.* 6:137–146 (1986).

Wong, D., et al., "Quantification of Neuroreceptors in the Living Human Brain. II. Inhibition Studies of Receptor Density and Affinity." *J. Cereb. Blood Flow Metab.* 6:147–153 (1986).

Zeeberg, B., et al. "Analysis of Three- and Four-Compartment Models for In Vivo Radioligand-Neuroreceptor Interaction." *Bull Math Biol.* 49(4):469–486 (1987).

a) 3-iodophenol, DEAD, PPh$_3$, THF, rt, 15h b) 2-methyl-4-iodophenol, DEAD, PPh$_3$, THF, rt, 15h c) 40%NHCH$_3$, ethanol, 130 °C, 3h d) HCl gas a) 3-Iodophenol, DEAD, PPh$_3$, THF, rt, 15h b) 2-methyl-4-iodophenol, DEAD, PPh$_3$, THF, rt, 15h c) 40%NHCH$_3$, ethanol, 130 °C, 3h d) HCl gas

5,320,825

SEROTONIN REUPTAKE INHIBITORS FOR S.P.E.C.T. IMAGING

FIELD OF THE INVENTION

This invention relates to novel compounds for CNS neurotransmitter systems, especially for the neurotransmitter serotonin, which can be utilized to image neurotransmitter reuptake systems in the brain.

BACKGROUND OF THE INVENTION

Depression, with its related conditions, is one of the most common mental disorders in the United States. It is estimated that about five percent of the adult population experiences a depressive episode in their lifetime that requires antidepressive drug therapy.

A chemical in the human brain, called serotonin, has been linked with depression and with other psychiatric disorders such as eating disorders, alcoholism, pain, anxiety and obsessive-compulsive behavior. Serotonin is a neural transmitter, a chemical that is used to send messages from one brain cell to another. Neurotransmitters bind to special receptor proteins in the membrane of nerve cells, like a key in a lock, triggering a chemical reaction within the cell. It has been found that drugs that enhance transmission of serotonin in the brain are useful in treating major psychiatric disorders such as depression. These drugs act as serotonin-uptake inhibitors.

Upon appropriate stimulation, the serotonin neuron in the brain releases serotonin. Once released, the serotonin is free for a short period of time before it is either metabolized or picked up again by another receptor protein on a serotonin neuron (called "serotonin reuptake"). Either metabolism or reuptake reduces the amount of free serotonin available. If reuptake is reduced, there is more serotonin available for transmission. Certain anti-depressive drugs, such as Prozac, operate to inhibit serotonin reuptake by binding with the serotonin receptor protein, effectively blocking the binding of the protein with the serotonin. Although Prozac has been found to be an effective anti-depressant treatment, it has side effects which can be serious. Prozac is known to bind to the serotonin receptor protein, but the responses of patients can differ widely. Some patients experience greater binding than others. If a patient is not responding to Prozac treatment, there is currently no way to determine why that is the case. Frequently, the physician will simply administer greater doses of the drug, a practice which will not necessarily lead to better results and which can enhance undesirable side effects.

Other serotonin reuptake inhibitors are also known which tend to be better tolerated than tricyclic agents such as Prozac. The structures of several of these inhibitors, and their affinity constants for the serotonin reuptake system (5-HT) as well as for other neurotransmitter reuptake systems, norepinephrine (NE) and dopamine (DA), are presented below in Table 1.

TABLE 1

Inhibition of Monoamine Uptake by Antidepressants in Rat Synaptosomes (Ki in nM)

| Compound | | DA | NE | 5-HT |
|---|---|---|---|---|
| 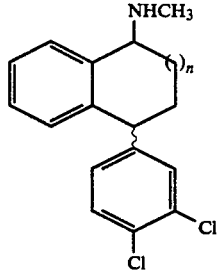 cis, 1S, 4S, n = 1 Sertraline | | 520 | 720 | 70 |
| 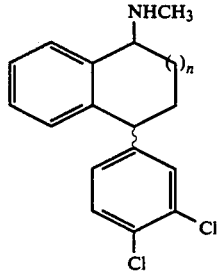 trans, 1R, 4S, n = 1 Tametraline | | 60 | 20 | 50 |
| 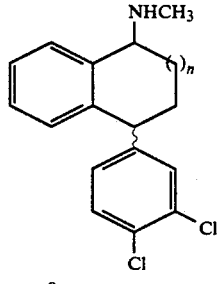 n = 0 Indatraline | trans<br>cis | 2000<br>860 | 90<br>34 | 0.58<br>0.03 |
| 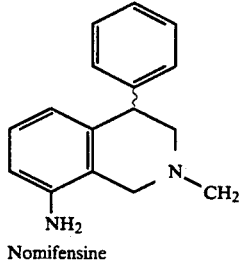 Nomifensine | | 48 | 5 | 5000 |
| 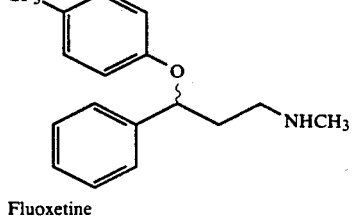 Fluoxetine | | 1590 | 289 | 25 |

TABLE 1-continued

Inhibition of Monoamine Uptake by Antidepressants in Rat Synaptosomes (Ki in nM)

| Compound | DA | NE | 5-HT |
|---|---|---|---|
| 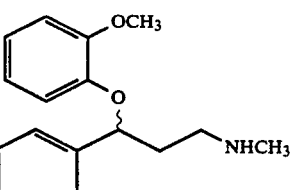 Nisoxetine | 365 | 670 | 3.8 |
| 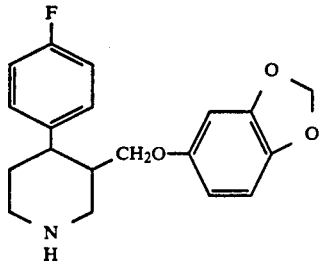 Paroxetine | — | 350 | 1.1 |

Although therapy with several of these drugs may not be accompanied by side effects as serious as those sometimes attributed to Prozac, there is still a need for a method to monitor the treatment of patients with the drugs as well as a method for studying the efficacy of such drugs.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made. By using these imaging methods to monitor the serotonin reuptake sites, improved treatment of patients with psychiatric disorders such as depression should be possible.

SUMMARY OF THE INVENTION

This invention relates to novel compounds of Formula

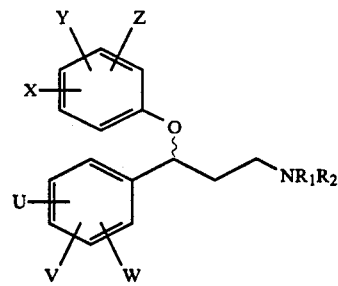

where each of U, V, W, X, Y and Z is independently selected from the group consisting of hydrogen; halogen; $C_1$-$C_4$ alkyl; $C_1$-$C_4$ alkyl substituted with one or more moieties selected from halogen atoms and hydroxy groups; $C_1$-$C_4$ alkoxy; $C_1$-$C_4$ alkoxy substituted with one or more moieties selected from halogen atoms and hydroxy groups; $C_1$-$C_6$ heterocycles; $C_1$-$C_4$ thioalkyl; $NR_3R_4$; —$R_5$—A—$R_6$; and —A—$R_7$; CN; $SO_2R_8$; —$NHCONH_2$; and $C(O)NR_3R_4$;

each of $R_1$, $R_2$, $R_3$ and $R_4$ is independently selected from the group consisting of hydrogen and $C_1$-$C_4$ alkyl;

each of $R_5$ and $R_6$ is independently a $C_1$-$C_6$ alkyl;

$R_7$ is selected from the group consisting of H, $C_1$-$C_6$ alkyl, $C_1$-$C_6$ heterocycles or —A—$R_5$;

$R_8$ is selected from the group consisting of $C_1$-$C_4$ alkyl and $NR_3R_4$;

A is selected from the group consisting of S, N and O;

provided that at least one of U, V, W, X, Y and Z is a halogen atom;

and pharmaceutically acceptable salts thereof.

As used herein, the term "alkyl" is intended to encompass straight-chained, branched and cyclic alkyl groups. Similarly, the terms "alkoxy" and "thioalkyl" encompass straight-chained and branched group. The term "heterocycle" is used to encompass ring structures in which one or more of the atoms in the ring is an element other than carbon, for example, sulfure, nitrogen or oxygen.

Tests suggest that the compounds of Formula I bind to neurotransmitter reuptake sites, and that many of the compounds are specific to serotonin reuptake sites. When the halogen atom on the molecule is a radioactive ion, such as $^{123}$I, the serotonin reuptake sites may be imaged by means such as PET and SPECT. Such imaging of the human brain may provide or suggest direct information on the location and quantitation of the reuptake sites. Direct assessment on the status of serotonin reuptake may provide evidence of how the selective serotonin reuptake inhibitors regulate the reuptake sites and may also be a diagnostic tool for individualizing the dosage for this class of antidepressants. The compounds of Formula I where the halogen atom is not a radioactive isotope will also bind to serotonin reuptake sites, suggesting therapeutic utility or use in in vitro binding studies. Certain of the compounds are also useful as intermediates for preparing the radioactive ion-labelled compounds.

Also included within the scope of this invention are certain novel intermediates of Formula II:

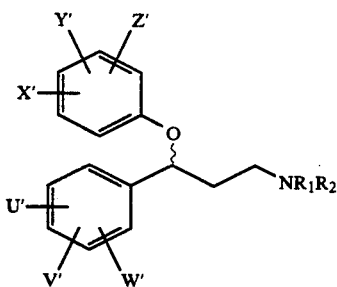

II where one of U', V', W', X', Y' and Z' is selected from the group consisting of Sn(R)$_3$, Si(R)$_3$ and HgR, where R is C$_1$-C$_5$ alkyl; and the others are selected from the group consisting of hydrogen; halogen; C$_1$-C$_4$ alkyl; C$_1$-C$_4$ alkyl substituted with one or more moieties selected from halogen atoms and hydroxy groups; C$_1$-C$_4$ alkoxy; C$_1$-C$_4$ alkoxy substituted with one or more moieties selected from halogen atoms and hydroxy groups; C$_1$-C$_6$ heterocycles; C$_1$-C$_4$ thioalkyl; NR$_3$R$_4$; —R$_5$ —A —R$_6$; and —A—R$_7$; CN; SO$_2$R$_8$; —NHCONH$_2$; and C(O)NR$_3$R$_4$; and where R$_1$-R$_8$ and A are as defined above.

DETAILED DESCRIPTION OF THE INVENTION

The novel compounds of Formulas I and II can exist in pure isomeric form or in racemic mixtures; this invention is contemplated to encompass the compounds in either form.

Figure 1:
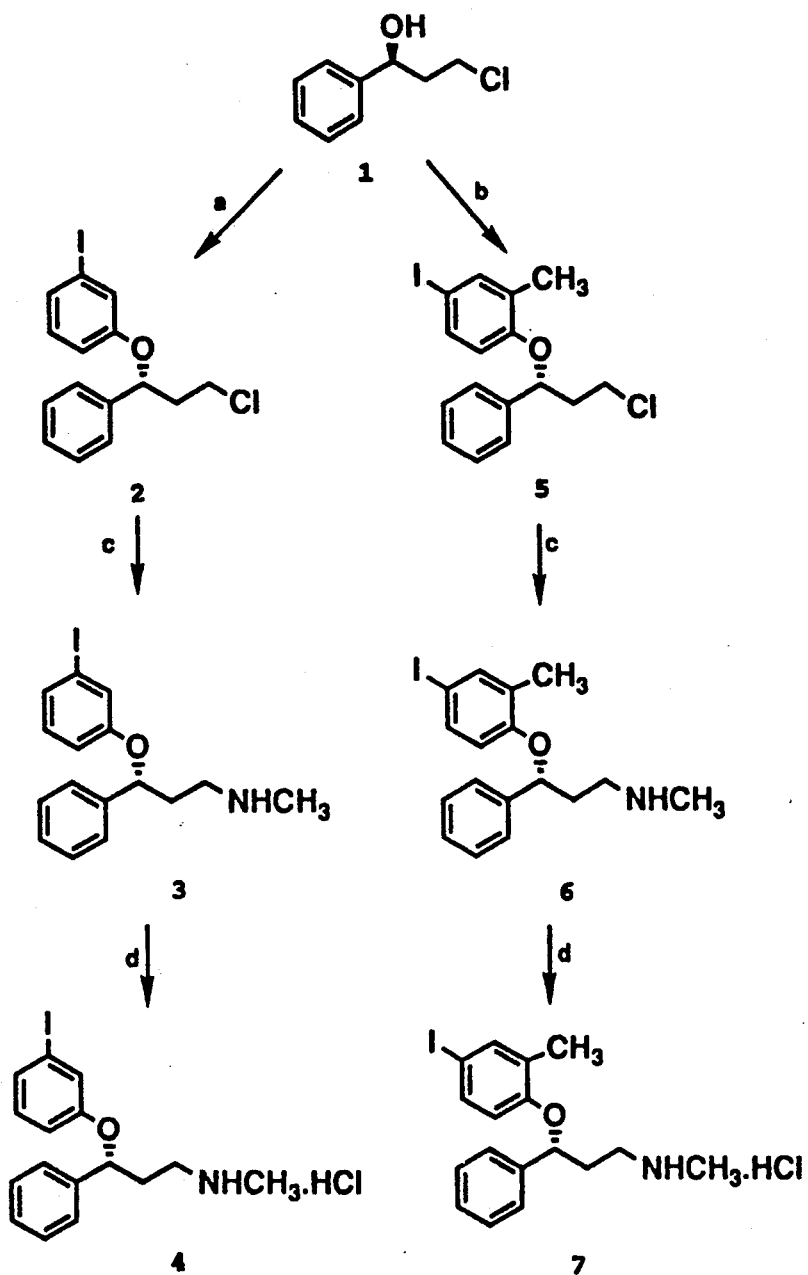
FIG. 1 is a schematic illustrating a method for preparing certain (R) isomers of compounds of this invention.
Figure 2:
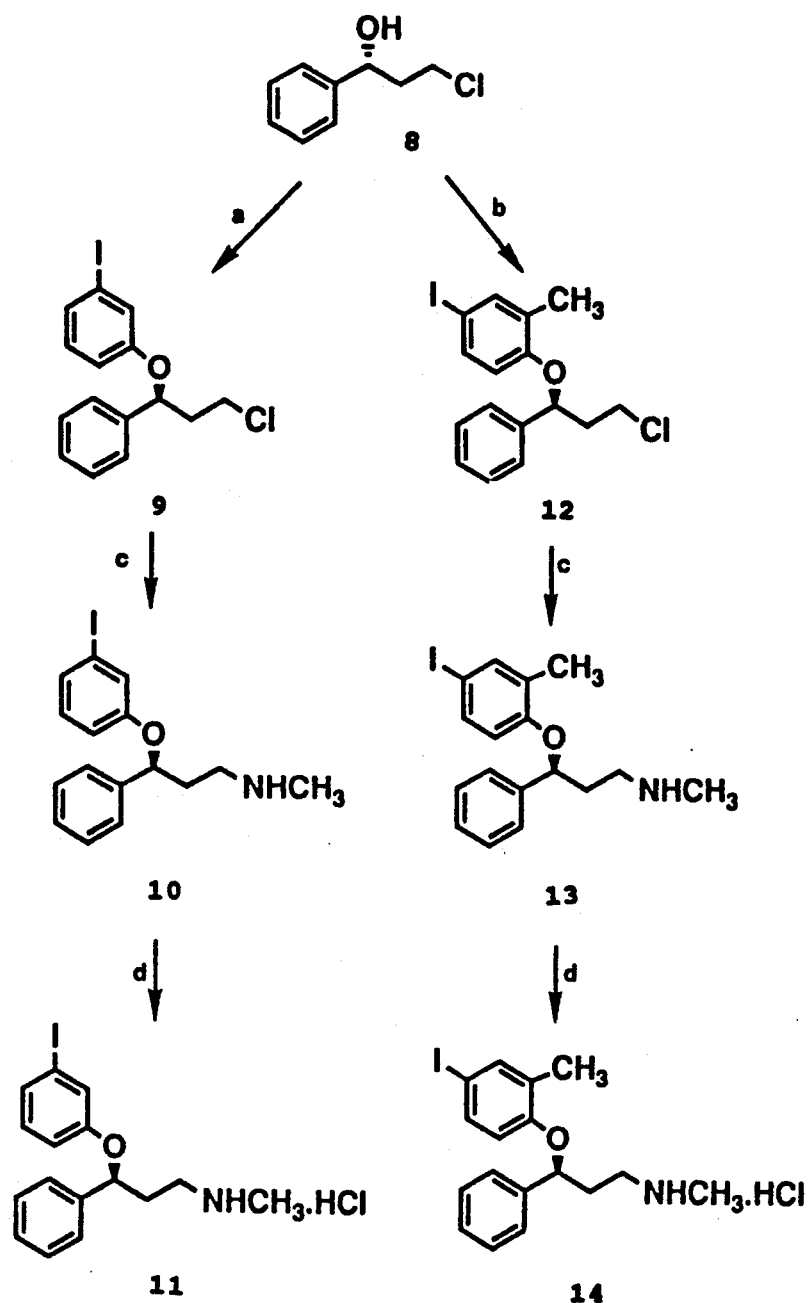
FIG. 2 is a schematic illustrating a method for preparing certain (S) isomers of compounds of this invention.

The compounds can be prepared by methods analogous to those illustrated in FIGS. 1 and 2 and described in the examples. Generally, a suitably substituted phenol

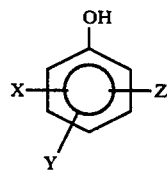

is condensed with 3-chloro-1-phenylpropanol or a substituted version thereof

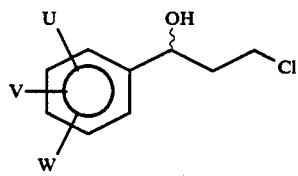

to yield a substituted 1-chloro-3-phenyl-3-phenoxypropane. Upon reaction of this product with the appropriate amine, HNR$_1$R$_2$, the desired compound of Formula I is obtained. Pharmaceutically acceptable salts, such as bromide or chloride salts, can be prepared by methods known in the art.

Compounds of Formula I labeled with an iodide isotope can be prepared from the corresponding bromocompound via the intermediacy of a stable, versatile tin intermediate. The bromine moiety is converted by a refluxing with dry triethylamine using tetrakistriphenylphosphine palladium catalyst. The resulting tributyltin compound can be converted to the desired iodo derivative by simply stirring with iodine in dry chloroform at room temperature. Alternatively, the tributyltin compound can be converted by reaction with the appropriate sodium iodide salt in aqueous hydrogen peroxide. The tributyltin compounds are not the only intermediates which can be used in preparing the radiolabeled compounds. Other intermediates within the scope of Formula II may be used in an analogous manner.

Although $^{125}$I isotopes are useful for laboratory testing, they will generally not be useful for actual diagnostic purposes because of the relatively long half-life (60 days) and low gamma-emission (30-65 KeV) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours).

Preferred compounds of this invention are those of Formula I wherein, simultaneously or independently: (1) one of X, Y and Z is alkyl; (2) one of X, Y and Z is halogen; (3) one of X, Y and Z is $^{123}$I; (4) R$_1$ is H and R$_2$ is CH$_3$. More preferred compounds of this invention are those of Formula I wherein, simultaneously or independently: (1) X is a 2-alkyl substituent; (2) Y is a 4-halogen substituent; (3) Z is hydrogen; (4) R$_1$ is H and R$_2$ is CH$_3$. The most preferred compounds are N-methyl-3-phenyl-3-(4-iodo-2-methylphenoxy)propylamine, and its pharmaceutically acceptable salts, preferably the (R)-(-)-isomer.

Specific examples of compounds contemplated within the scope of this invention are presented in Table 2.

TABLE 2

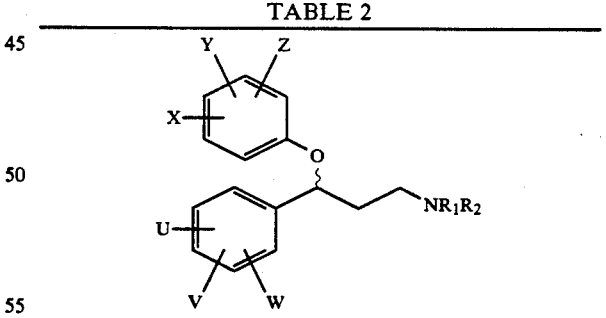

where R$_1$ and R$_2$ are independently selected from hydrogen, methyl, ethyl, n-propyl, n-butyl, cyclopropyl, i-propyl, i-butyl, t-butyl.

| X or U | Y or V | Z or W |
|---|---|---|
| 2-I | H | H |
| 3-I | H | H |
| 4-I | H | H |
| 2-I | 3-OH | H |
| 3-I | 2-OH | H |
| 4-I | 2-OH | H |
| 4-I | 3-OH | 2-Me |
| 2-I | 3-OH | 4-Me |
| 3-I | 2-OH | 4-Me |
| 4-I | 2-OH | 3-Me |

TABLE 2-continued

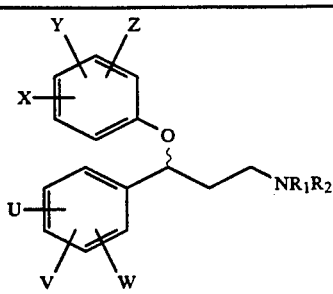

where R₁ and R₂ are independently selected from
hydrogen, methyl, ethyl, n-propyl, n-butyl, cyclopropyl,
i-propyl, i-butyl, t-butyl.

| X or U | Y or V | Z or W |
|---|---|---|
| 4-I | 3-CN | H |
| 2-I | 3-CN | H |
| 3-I | 2-CN | H |
| 4-I | 2-CN | H |
| 4-I | 3-CN | 2-Me |
| 2-I | 3-CN | 4-Me |
| 3-I | 2-CN | 4-Me |
| 4-I | 2-CN | 3-Me |
| 2-I | 3-Me | H |
| 3-I | 4-Me | H |
| 4-I | 2-Me | H |
| 2-I | 3-CF₃ | H |
| 3-I | 4-CF₃ | H |
| 4-I | 2-CF₃ | H |
| 2-I | 3-OMe | H |
| 3-I | 4-OMe | H |
| 4-I | 2-OMe | H |
| 2-I | 3-NH₂ | H |
| 3-I | 4-NH₂ | H |
| 4-I | 2-NH₂ | H |
| 2-I | 3-NHCH₃ | H |
| 3-I | 4-NHCH₃ | H |
| 4-I | 2-NHCH₃ | H |
| 2-I | 3-N(Me)₂ | H |
| 3-I | 4-N(Me)₂ | H |
| 4-I | 2-N(Me)₂ | H |
| 2-I | 3-NH₂ | H |
| 3-I | 4-NH₂ | H |
| 4-I | 2-NH₂ | H |
| 2-I | 4-NH₂ | H |
| 3-I | 2-NH₂ | H |
| 4-I | 3-NH₂ | H |
| 2-I | 3-SMe | H |
| 3-I | 4-SMe | H |
| 4-I | 2-SMe | H |
| 2-I | 3-OMe | 4-OMe |
| 3-I | 2-OMe | 4-OMe |
| 4-I | 2-OMe | 3-OMe |
| 2-I | 3-OMe | 4-OMe |
| 3-I | 2-OMe | 4-OMe |
| 4-I | 2-OMe | 3-OMe |
| 2-I | 3-CH₂CH₂F | H |
| 3-I | 4-CH₂CH₂F | H |
| 4-I | 2-CH₂CH₂F | H |
| 2-I | 3-OCH₂CH₂F | H |
| 3-I | 4-OCH₂CH₂F | H |
| 4-I | 2-OCH₂CH₂F | H |
| 2-I | 3-CH₃ | 4-CH₃ |
| 3-I | 4-CH₃ | 3-CH₃ |
| 4-I | 2-CH₃ | 4-CH₃ |
| 2-I | 3-OCH₂CH₃ | CH₃ |
| 3-I | 4-OCH₂CH₃ | CH₃ |
| 4-I | 2-OCH₂CH₃ | CH₃ |
| 2-I | 3-CH₃ | OH |
| 3-I | 4-CH₃ | OH |
| 4-I | 2-CH₃ | OH |
| 2-I | 3-CF₃ | OH |
| 3-I | 4-CF₃ | OH |
| 4-I | 2-CF₃ | OH |
| 2-I | 3-CH₃ | 4-OCH₃ |
| 3-I | 4-CH₃ | 2-OCH₃ |
| 4-I | 2-CH₃ | 3-OCH₃ |

TABLE 2-continued

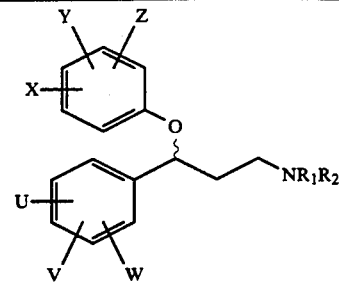

where R₁ and R₂ are independently selected from
hydrogen, methyl, ethyl, n-propyl, n-butyl, cyclopropyl,
i-propyl, i-butyl, t-butyl.

| X or U | Y or V | Z or W |
|---|---|---|
| 2-I | 3-CF₃ | 4-OCH₃ |
| 3-I | 4-CF₃ | 3-OCH₃ |
| 4-I | 2-CF₃ | 2-OCH₃ |
| 2-I | 3-OCH₃ | 4-OCH₃ |
| 3-I | 4-OCH₃ | 2-OCH₃ |
| 4-I | 2-OCH₃ | 3-OCH₃ |
| 2-I | 3-Cl | 4-CH₃ |
| 3-I | 4-Cl | 2-CH₃ |
| 4-I | 2-Cl | 3-CH₃ |
| 2-I | 3-CH₃ | 4-Cl |
| 3-I | 4-CH₃ | 2-Cl |
| 4-I | 2-CH₃ | 3-Cl |
| 2-I | 3-F | 4-CH₃ |
| 3-I | 4-F | 2-CH₃ |
| 4-I | 2-F | 3-CH₃ |
| 2-I | 3-CH₃ | 4-F |
| 3-I | 4-CH₃ | 2-F |
| 4-I | 2-CH₃ | 3-F |

(In this Table, the numerical prefix is intended to indicate placement of substitution on either ring of the compound.)

The compounds of this invention lend themselves easily to formation from materials which could be provided to users in kits. Kits for forming the imaging agents can contain, for example, a vial containing a physiologically suitable solution of an intermediate of Formula II in a concentration and at a pH suitable for optimal complexing conditions. The user would add to the vial an appropriate quantity of the radioisotope, e.g., Na$^{123}$I, an oxidant, such as hydrogen peroxide. The resulting labelled ligand may then be administered intravenously to a patient, and receptors in the brain imaged by means of measuring the gamma ray or photo emissions therefrom.

The following examples are illustrative, but not limiting, of the present invention.

Melting points were determined with a Meltemp (Laboratory Devices) and are reported uncorrected. Infrared spectra were obtained with a Mattson Polaris FT-IR spectrometer. NMR spectra were determined with a Varian EM 360A spectrometer. Elemental analyses were performed by Atlantic Microlabs, Inc., of Atlanta, Ga. All of the chemicals were of reagent grade and used without further purification.

EXAMPLE 1

Preparation of
[R]-(-)-N-Methyl-3-phenyl-3-(3-iodophenoxy)propylamine (Compound 4, FIG. 1)

Triphenylphosphine (1.54 g, 5.88 mmole) and ethyl azodicarboxylate (8.93 mL, 1.03 g, 5.88 mmol) were added to a solution of [S]-3-chloro-1-phenylpropanol (1.0 g, 5.88 mmol) and 3-iodophenol at room temperature for 15 hours. THF was removed under aspirator vacuum. The residue was triturated with petroleum ether (3×15 mL). The combined fractions were concentrated, and the crude product was purified by flash column chromatography on silica gel. Elution with petroleum ether and removal of solvent afforded 1.64 g (75%) of [R]-(+)-11-chloro-3-phenyl-3-(3-iodophenoxy)propane, Compound 2, as a thick colorless liquid: $[\alpha]^{25}_D$+1.85 (c 5.4, CHCL$_3$); $^1$H NMR (CDCL$_3$ 250 MHz)δ 7.40-7.20 (m, 7H), 6.90-6.76 (m, 2H), 5.34 (dd, J=4.6, 9.2 Hz, 1H), 3.82-3.72 (m, 1H), 3.62-3.53 (m, 1H), 2.51—2.38 (m, 1H), 2.26-2.14 (m, 1H). Anal. C$_{15}$H$_{14}$Cl I O; C,H.

In a sealed tube, a mixture of Compound 2 (0.56 g, 1.50 mmol), aqueous methylamine (40%, 4 mL) and ethanol (1.5 mL) was heated at 130° C. for 3 hours. The cooled mixture was poured into water (5 mL) and was extracted with CH$_2$CL$_2$ (3×5 mL). The organic solution was dried, filtered and concentrated to give a yellowish oil. Flash-column chromatography of the crude produce on silica gel (5% MeOH/CH$_2$Cl$_2$) afforded 0.28 g (51%) of [R]-(-)-N-Methyl-3-phenyl-3-(3-iodophenoxy)propylamine (Compound 3) as a pale yellow oil; R$_f$ 0.29 (10% MeOH/CH$_2$Cl$_2$); $[\alpha]^{25}_D$-0.71 (c 1.83, CHCl$_3$); $^1$H NMR (CDCl$_3$, 250 MHz) δ 7.35-7.15 (m, 7H), 6.90-6.72 (m, 2H), 5.23 (dd, J=4.6, 8.5 Hz, 1H) 3.50 (br s, 1H), 2.81 (br t, 1H), 2.48 (br s, 3H), 2.30-2.16 (m, 1H), 2.16-2.03 (m, 1H); FTIR (neat) 3400 (br, NH), 3100-300 (ArH), 29500-2750 (CH), 1575, 1475, 1225 cm$^{-1}$. MS m/1 367 (M+1).

HCl gas was bubbled through a solution of Compound 3 in a minimum amount 1:1 ether: CH$_2$Cl$_2$. The cloudy solution was evaporated into dryness to give quantitatively the title compound (Compound 4) as a hygroscopic solid: mp 64° C. $[\alpha]^{25}_D$-15.39 (c 1.37, CHCl$_3$); $^1$H NMR CDCl$_3$, 250 MHz)δ 9.61 (br s, 2H), 7.35-7.18 (m, 7H), 6.90-6.72 (m, 2H), 5.32 (dd, J=4.7, 8.5 Hz, 1H), 3.10 (m, 2H), 2.65 (br t, 3H), 2.41 (m, 2H).

EXAMPLE 2

Preparation of
[R]-(-)-N-Methyl-3-phenyl-3-(4-iodo-2-methylphenoxy)propylamine hydrochloride (Compound 7)

The compound [R]-(+)-1-chloro-3-phenyl-3-(4-iodo-2-methylphenoxy)propane (Compound 5) was prepared in the same manner as for the preparation of Compound 2 in Example 1, but using [S]-3-chloro-1-phenylpropanol (1.0 g, 5.88 mmol), 4-iodo-2-methylphenol (1.38 g, 5.88 mmol), triphenylphosphine (1.54 g, 5.88 mmol), and ethyl azodicarboxylate (0.93 mL, 1.04 g, 5.88 mmol) in THF (15 mL) at room temperature for 15 hours. Workup and purification gave 1.60 g (70%) of Compound 5 as a thick pale yellow liquid: $[\alpha\pi^{25}_D$+14.02 (c 7.7, CHCL$_3$); $^1$H NMR (CDCl$_3$, 250 MHz) δ 7.41-7.20 (m, 7H), 6.39 (d, J=8.8 Hz, 1H), 5.34 (dd, J=4.4, 8.8 Hz, 1H), 3.81-3 72 (m, 1H), 3.63-3.55 (m, 1H), 2.55-2.41 (m, 1H), 2.31-2.16 (m, 1H), 2.7 (s, 3H); FTIR (neat) 3080, 3020, 2970, 2915, 1585, 1485(s), 1450, 1390, 1360, 1290, 1245(s), 1180, 1130 cm$^{-1}$. Anal. C$_{17}$H$_{20}$INO: C,H.

The method for preparation of Compound 4 in Example 1 was modified. A mixture of Compound 5 (0.58 g, 1.5 mmol), aqueous methylamine (40%, 4 mL) and ethanol (1.5 mL) in a sealed tube was heated at 130° C. for 3 hours. Workup and flash-column chromatography on silica gel (5% MeOH/CH$_2$Cl$_2$) afforded 0.25 g (44%) of [R]-(-)-N-methyl-3-phenyl-3-(4-iodo-2-methylphenoxy)propylamine (Compound 6) as a pale yellow oil: R$_f$ 0.36 (12% MeOH/CH$_2$Cl$_2$); $[\alpha]^{25}_D$+11.98 (C 3.32, CHCl$_3$): $^1$H NMR (CDCl$_3$, 250 MHz) δ 7.43-7.20 (m, 7H), 6.38 (d, J=5.4 Hz, 1H); 5.23 (dd, J=3.0, 5.4 Hz, 1H), 2.78 (br t, 2H), 2.45 (br s, 3H), 2.28 (2, 3H), 2.28-2.12 (m, 1H), 2.10-2.00 (m 1H).

HCl was bubbled through a solution of Compound 6 in a minimum amount of 1:1 ether/CH$_2$Cl$_2$. Removal of the solvent afforded a quantitative yield of the title compound (Compound 7) as a hygroscopic solid: mp 68° C. $[\alpha]^{25}_D$-8.34 (c 0.82, CHCl$_3$): $^1$H NMR (CDCl$_3$, 250 MHz) δ 9.66 (br s, 2H), 7.41-7.19 (m, 7H), 6.38 (d, J=8.8 Hz, 1H), 5.39 (dd, J=4.4, 8.0 Hz, 1H), 3.12 (m, 2H), 2.61 (br t, 2H), 2.49 (m, 2H), 2.25 (s, 3H). Anal. C$_{17}$H$_{21}$ClINO: C, H, N.

EXAMPLE 3

Preparation of
[S]-(+)-N-Methyl-3-phenyl-3-(3-iodophenoxy)propylamine (Compound 11)

The compound [S]-(-)-1-chloro-3-phenyl-3-(3iodophenoxy)propane (Compound 9) was prepared in the same manner as for preparation of Compound 2 in Example 1 but using [R]-3-chloro-1-phenylpropanol (1.0 g, 5.88 mmol). Workup and purification gave 1.70 g (78%) of Compound 9 as a thick colorless liquid: $[\alpha]^{25}_D$-0.61 (c 6.55, CHCl$_3$); $^1$H NMR; (CDCl$_3$), 250 MHz δ 7.37-7.14 (m, 7H), 6.90-6.75 (m, 2H), 5.33 (dd, J=4.4, 8.7 Hz, 1H), 3.81-3.71 (m, 1H), 3.61-3.51 (m, 1H), 2.51-2.36 (m, 1H), 2.25-2.11 (m, 1H); IR (neat) 3090, 3070, 2980, 2900, 1580(s), 1470(s), 1410, 1360, 1280, 1220, 1160; spectra are the same as for Compound 2.

Compound 11 was prepared in the same manner as Compound 4. A mixture of Compound 9 (0.56 g, 1.50 mmol), aqueous methylamine (40%, 4mL), and ethanol (1.5 mL) in a sealed tube was heated at 130° C. for three hours. After workup and flash-column chromatography (5% MeOH/CH$_2$Cl$_2$), the compound [S]-(+)-N-methyl-3-phenyl-3-(3-iodophenoxy)propylamine (Compound 10) (0.31 g, 57%) was obtained as a pale yellow oil: R$_f$ 0.49 (10% MeOH/CH$_2$Cl$_2$); $[\alpha]^{25}_D$-1.61 (c 1.06, CHCl$_3$); $^1$H NMR (CDCl$_3$, 250 MHz) δ 7.37-7.19 (m, 7H), 6.90-6.75 (m, 2H), 5.22 (dd, J=4.6, 8.5 Hz, 1H), 2.78 (br t, 2H), 2.45 (br s, 3H), 2.27-2.12 (m, 1H), 2.08-1.95 (m, 1H). FTIR (neat) 3400 (br, NH), 3100-300 (ArH), 2950-2750 (CH), 1590, 1460, 1226 cm$^{-1}$.

HCl gas was bubbled through a solution of Compound 10 in a minimum amount of 1:1 ether/CH$_2$Cl$_2$. Removal of the solvent afforded a quantitative yield of the title compound (Compound 11) as a hygroscopic solid: mp 62° C. $[\alpha]^{25}_D$+16.42 (C 2.12, CHCl$_3$); $^1$H NMR (CDCl$_3$, 250, MHz) δ 9.63 (br s, 2H), 7.35-7.18 (m, 7H), 6.89-6.72 (m, 2H), 5.32 (dd, J=4.7, 8.5 Hz, 1H), 3.21 (m, 2H), 2.63 (br t, 3H), 2.42 (m, 2H): Anal. C$_{16}$H$_{18}$NIO: C, H, N.

EXAMPLE 4

Preparation of
{S}-(+)-N-Methyl-3-phenyl-3-(4-iodo-2-methylphenoxy)propylamine hydrochloride (Compound 14)

The compound [S]-(-)-1-chloro-3-phenyl-3-(4-iodo-2-methylphenoxy)propane (Compound 12) was prepared in the same manner as Compound 2 in Example 1 but using [R]-3-chloro-1-phenylpropanol (1.0 g, 5.88 mmol), 4-iodo-2-methylphenol (1.38 g, 5.88 mmol), triphenylphosphine (1.54 g, 5.88 mmol) and ethyl azodicarboxylate (0.93 mL, 1.04 g, 5.88 mmol) in THF (15 mL) at room temperature for 15 hours. Workup and purification gave 1.58 g (69%) of Compound 12 as a thick pale yellow liquid: $[\alpha]^{25}_D+14.97$ (c 10.73, CHCl$_3$); $^1$H NMR (CDCl$_3$, 250 MHz) δ 7.42–7.20 (m, 7H), 6.39 (d, J=8.8 Hz, 1H), 5.34 (dd, J=4.6, 8.8 Hz, 1H), 3.83–3.73 (m, 1H), 3.65–3.55 (m, 1H), 2.55–2.40 (m, 1H), 2.29–2.13 (m, 1H), 2.25 (s, 3H), FTIR (neat) 3050, 3015, 2950, 2900, 1600, 1480 (s), 1460, 1395, 1350, 1300, 1250(s), 1200, 1135 cm$^{-1}$. Anal C$_{17}$H$_{20}$INO; C, H.

A mixture of Compound 12 (0.58 g, 1.50 mmol), aqueous methylamine (40%, 4 mL), and ethanol (150 mL) in a sealed tube was heated at 130° C. for three hours. Workup and chromatography on silica gel (5% MeOH/CH$_2$Cl$_2$) afforded 0.27 g (48%) of [S]-(+)-N-methyl-3-phenyl-3-(4-iodo-2-methylphenoxy)propylamine (Compound 13) as a yellowish oil: R$_f$ 0.25 (8% MeOH/CH$_2$Cl$_2$); $[\alpha]^{25}_D$-11.5 (C 3.03, CHCl$_3$); $^1$H NMR (CDCl$_3$, 250 MHz) δ 7.43–7.19 (m, 7H), 6.37 (d, J=5.4 Hz, 1H), 5.23 (dd, J=3.0, 5.4 Hz, 1H), 2.78 (br s, 2H), 2.45 (br s, 3H), 2.27 (s, 3H), 2.27–2.11 (m, 1H), 2.11–1.97 (m, 1H); FTIR (neat), 3400 (NH), 300–2550, 14990, 1250 cm$^{-1}$.

HCl gas was bubbled through a solution of Compound 13 in a minimum amount of 1:1 ether/CH$_2$Cl$_2$. The cloudy solution was evaporated into dryness to give quantitatively the title compound (Compound 14) as a hygroscopic solid: mp 66° C. $[\alpha]^{25}_D$+6.43 (c 1.14, CHCl$_3$); $^1$H NMR (CDCl$_3$, 250 MHz) δ 9.68 (br s, 2H), 7.40–7.18 (m, 7H), 6.37 (d, J=8.8 Hz, 1H), 5.38 (dd, J=4.4, 8.0 Hz, 1H), 3.12 (br s, 2H), 2.60 (br t, 3H), 2.49 (m, 2H), 2.22 (s, 3H). MS. m/1 381 (M+1).

EXAMPLE 4

The affinity of the compounds prepared in Examples 1–4 to serotonin and norepinephrine uptake sites was studied using in vitro competitive binding assays. The results are presented in Table 3.

TABLE 3

| Competiton of serotonin and norepinephrine reuptake sites in rat brain tissue preparation | | |
|---|---|---|
| Compound | Serotonin Uptake [$^3$H]-Paroxetine K$_i$ (nM) | Norepinephrine Uptake [$^3$H]-Nisoxetine IC$_{50}$ (nM) |
| 4 | 0.8 | 500 |
| 11 | 8.2 | 7000 |
| 7 | 5.0 | 20 |
| 14 | 0.8 | 9 |

There are several basic requirements for serotonin reuptake inhibitors as in vivo SPECT imaging agents. First, they should desirably be labeled with a suitable short-lived isotope emitting a medium energy gamma ray (100–300 KeV) and should be capable of being synthesized and purified rapidly. The compounds of this invention can be labeled with $^{123}$I, an isotope emitting gamma energy of 159 KeV, as described previously. Second, they should be able to pass through the intact blood-brain barrier following intravenous injection. The compounds of this invention are neutral and lipid-soluble molecules. Preliminary studies of related compound radioiodinated fluoxetine showed good initial brain uptake and prolonged brain retention (0.68% and 0.63% dose/organ at two minutes and 8 hours, respectively). These results suggest that the compounds of this invention are feasible candidates as imaging agents for the central nervous system. Third, the compounds should exhibit high affinity and low nonspecific binding to the receptor. The test results provided in Example 4 suggest that the compounds of this invention meet this requirement.

EXAMPLE 5

The biodistribution of [R]-(-)-N-methyl-3-phenyl-3-(4-$^{123}$I-2-methylphenoxy)propylamine hydrochloride (compound 7) in rats, after intravenous injection, was analyzed. Results are presented in Table 4 and indicate that moderate brain uptake (0.64–0.84% dose/organ) is found consistently throughout the two hour period.

TABLE 4

| Biodistribution in rats after an iv injection (% dose/organ) (n = 3) | | | | |
|---|---|---|---|---|
| Organ | | | | |
| Blood | 4.15 ± 0.30 | 2.19 ± 0.32 | 2.19 ± 0.11 | 2.39 ± 0.33 |
| Heart | 2.88 ± 0.14 | 0.55 ± 0.04 | 0.39 ± 0.02 | 0.32 ± 0.015 |
| Muscle | 9.05 ± 1.20 | 22.77 ± 4.86 | 21.49 ± 2.44 | 19.63 ± 1.89 |
| Lung | 18.26 ± 1.70 | 9.36 ± 1.52 | 9.11 ± 0.48 | 6.81 ± 0.76 |
| Kidney | 6.07 ± 1.03 | 2.70 ± 0.48 | 1.88 ± 0.13 | 1.12 ± 0.44 |
| Spleen | 0.48 ± 0.38 | 1.09 ± 0.32 | 1.05 ± 0.08 | 0.79 ± 0.05 |
| Liver | 15.61 ± 3.34 | 23.56 ± 3.61 | 22.12 ± 1.74 | 24.52 ± 1.82 |
| Skin | 7.37 ± 0.49 | 6.75 ± 1.35 | 9.39 ± 1.30 | 6.92 ± 0.83 |
| Thyroid | 0.094 ± 0.023 | 0.07 ± 0.02 | 0.06 ± 0.02 | 0.04 ± 0.008 |
| Brain | 0.64 ± 0.08 | 0.80 ± 0.04 | 0.84 ± 0.051 | 0.68 ± 0.01 |

EXAMPLE 6

Preparation and Testing of Iodo-Fluoxetine (I-FXT)

Figure 3:
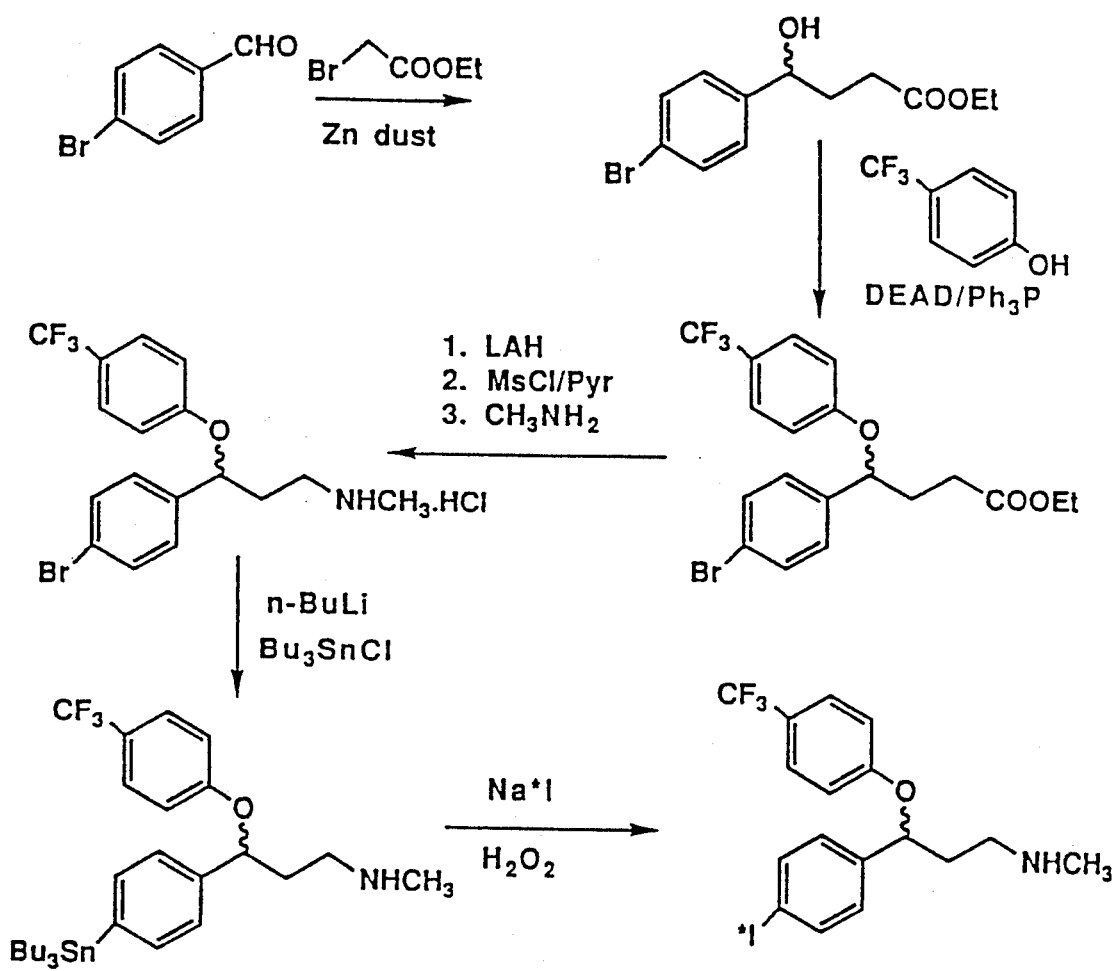
FIG. 3 is a schematic illustrating a method for preparing the compound iodo-fluoxetine.

The compound iodo-fluoxetine (Compound 15) was prepared via the synthesis illustrated in FIG. 3. The hydrogen peroxide catalyzed iododestannylation gave [$^{125}$I]I-FXT in high yield (70%) and excellent purity (≥96%, HPLC). The biodistribution in rats (Table 5) showed good initial brain uptake and prolonged brain retention (0.68% and 0.63% dose/organ at 2 min. and 8 hr., respectively). High heart uptake was also observed with initial uptake of 2.3% at 2 min. and 0.3% at 8 hr. post injection. However, ex vivo autoradiography of rat brain sections at 2 hr. post i.v. injection showed a regional distribution pattern, which was not altered by pretreatment of paroxetine (10 mg/Kg, i.p.). In vitro binding studies indicated strong non-specific binding with prefrontal cortex membrane of rat brain. These data suggest that further animal studies of I-FXT are needed to identify the nature of in vivo brain uptake and retention.

| Biodistribution in rats after an iv injection (% dose/organ) | | | |
|---|---|---|---|
| Organ | 2 min. | 15 min. | 60 min. |
| Blood | 3.03 ± 0.40 | 1.71 ± 0.31 | 3.16 ± 0.36 |
| Heart | 2.27 ± 0.31 | 1.14 ± 0.04 | 0.43 ± 0.05 |
| Muscle | 12.71 ± 5.3 | 16.01 ± 4.55 | 22.63 ± 4.48 |
| Lung | 11.09 ± 2.32 | 6.77 ± 0.25 | 7.32 ± 0.45 |
| Kidney | 4.16 ± 0.36 | 4.05 ± 0.44 | 2.32 ± 0.38 |
| Spleen | 0.61 ± 0.06 | 0.93 ± 0.15 | 1.20 ± 0.13 |
| Liver | 15.92 ± 2.41 | 16.27 ± 2.35 | 17.64 ± 1.88 |
| Skin | 4.90 ± 0.50 | 5.84 ± 0.95 | 10.76 ± 2.85 |
| Thyroid | 0.10 ± 0.04 | 0.07 ± 0.03 | 0.08 ± 0.01 |
| Brain | 0.61 ± 0.12 | 0.68 ± 0.02 | 0.78 ± 0.01 |
| Organ | 120 min. | 240 min. | 480 min. |
| Blood | 3.62 ± 0.24 | 4.99 ± 0.70 | 7.61 ± 1.11 |
| Heart | 0.48 ± 0.02 | 0.28 ± 0.01 | 0.32 ± 0.03 |

| Biodistribution in rats after an iv injection (% dose/organ) | | | |
|---|---|---|---|
| Muscle | 24.22 ± 0.68 | 20.38 ± 2.67 | 19.90 ± 2.61 |
| Lung | 7.21 ± 0.36 | 7.57 ± 2.36 | 5.00 ± 0.46 |
| Kidney | 1.82 ± 0.21 | 1.18 ± 0.17 | 1.11 ± 0.06 |
| Spleen | 1.09 ± 0.07 | 0.71 ± 0.11 | 0.52 ± 0.048 |
| Liver | 11.55 ± 0.78 | 11.52 ± 0.91 | 16.47 ± 2.03 |
| Skin | 10.08 ± 0.78 | 8.27 ± 0.75 | 10.78 ± 0.07 |
| Thyroid | 0.10 ± 0.02 | 0.14 ± 0.001 | 0.22 ± 0.06 |
| Brain | 0.84 ± 0.073 | 0.70 ± 0.031 | 0.61 ± 0.07 |

What is claimed is:

1. Compounds of the formula

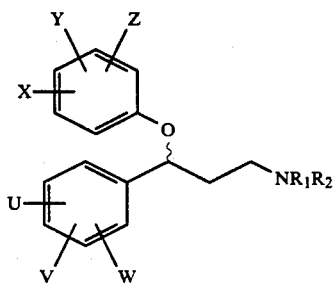

where
each of U, V, W and Z is a hydrogen atom;
X is an iodine atom in the para-position;
Y is a $C_1$-$C_4$ alkyl group in the ortho-position;
$R_1$ and $R_2$ are independently selected from the group consisting of hydrogen and $C_1$-$C_4$ alkyl;
and pharmaceutically acceptable salts thereof.

2. Compounds of claim 1 where X is $^{123}$I.
3. Compounds of claim 1 where Y is methyl.
4. Compounds of claim 3 where $R_1$ is H and $R_2$ is $CH_3$.
5. Compounds of claim 1 where $R_1$ is H and $R_2$ is $CH_3$.
6. The compound of claim 1 which is R-N-methyl-3-phenyl-3-(4-iodo-2-methylphenoxy)propylamine.
7. The compound N-methyl-3-phenyl-3-(4-iodo-2-methylphenoxy)propylamine.
8. A serotonic receptor imaging agent comprising a compound of claim 1 wherein X is a radioactive iodine isotope.
9. A serotonic receptor imaging agent comprising a compound of claim 3 wherein X is an iodine isotope.
10. A serotonin receptor imaging agent comprising a compound of claim 5 wherein X is an iodine isotope.
11. A serotonin receptor imaging agent comprising a compound of claim 4 wherein X is an iodine isotope.
12. The compound of claim 7 wherein the iodine atom is an iodine isotope.
13. The compound of claim 6 wherein the iodine atom is an iodine isotope.
14. Compounds of the formula

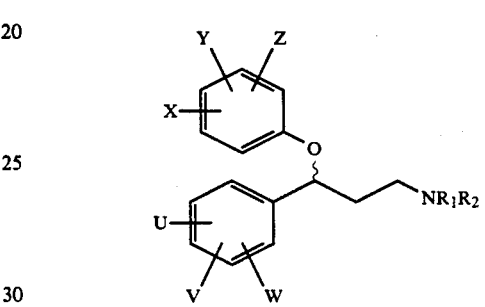

where
each of U, V, W, Y and Z is a hydrogen atom;
X is an iodine atom in the ortho-position;
$R_1$ and $R_2$ are independently selected from the group consisting of hydrogen and $C_1$-$C_4$ alkyl;
and pharmaceutically acceptable salts thereof.

15. Compounds of claim 14 where $R_1$ is H and $R_2$ is $CH_3$.
16. Compounds of claim 14 where X is a radioactive isotope.

* * * * *

UNITED STATES PATENT AND TRADEMARK OFFICE
CERTIFICATE OF CORRECTION

PATENT NO. : 5,320,825
DATED : June 14, 1994
INVENTOR(S) : Hank F. Kung

It is certified that error appears in the above-indentified patent and that said Letters Patent is hereby corrected as shown below:

At Column 9, line 55, please delete "$[a\pi^{25}{}_D$" and insert -- $[a]^{25}{}_D$ -- therefor.

At Column 12, line 52, please insert -- TABLE 5 --.

Signed and Sealed this

Sixteenth Day of May, 1995

Attest:

BRUCE LEHMAN

Attesting Officer

Commissioner of Patents and Trademarks